| United States Patent [19] | [11] Patent Number: 4,861,591 |
| Weierstall et al. | [45] Date of Patent: Aug. 29, 1989 |

[54] FORMULATIONS FOR HYGROSCOPIC PHARMACEUTICALS

[75] Inventors: Richard P. Weierstall; Robin P. Enever, both of Rouses Point; Kathleen L. Brunelle, Plattsburgh; Gerard F. Thone, Chazy, all of N.Y.; Ronald N. Warner, Morgantown, W. Va.

[73] Assignee: American Home Products Corporation, New York, N.Y.

[21] Appl. No.: 309,019

[22] Filed: Feb. 7, 1989

Related U.S. Application Data

[63] Continuation of Ser. No. 121,971, Nov. 18, 1987, abandoned.

[51] Int. Cl.$^4$ ............................................. A01N 59/06
[52] U.S. Cl. ..................................................... 424/690
[58] Field of Search ......................................... 424/155

[56] References Cited

U.S. PATENT DOCUMENTS

| 2,923,660 | 2/1960 | Hallmann | 423/600 |
| 3,843,778 | 10/1974 | Diamond et al. | 424/155 |
| 4,486,412 | 12/1985 | Shah et al. | 424/156 |

FOREIGN PATENT DOCUMENTS 1401360  7/1975  United Kingdom ................ 424/155

*Primary Examiner*—Curtis R. Davis
*Attorney, Agent, or Firm*—John W. Routh

[57] ABSTRACT

There are provided pharmaceutical dosage forms for oral administration comprising a gelatin capsule encapsulating an admixture of at least one solid hygroscopic medicinal substance, which would otherwise disturb the gastric tract balance, with an at least partially hydrogenated and/or solidified vegetable oil.

7 Claims, No Drawings

FORMULATIONS FOR HYGROSCOPIC PHARMACEUTICALS

This application is a continuation of application Ser. No. 121,971, filed Nov. 18, 1987, now abandoned.

This invention relates to formulations for solid hygroscopic pharmaceutical materials which tend to cause disturbances in the balance of the gastrointestinal tract, particularly the stomach, when administered orally to animals including humans. More particularly the invention relates to formulations for a hygroscopic pharmaceutical material, such as an acidified antacid composition, with at least a partially hydrogenated and/or solidified vegetable oil, enclosed in a gelatin capsule.

BACKGROUND OF THE INVENTION

Oral administration of solid hygroscopic pharmaceutical materials can cause disturbances in the balance of the gastrointestinal tract, particularly in the stomach, where the drug is ingested for its pharmaceutical effects. In some instances and in some animals, the disturbance takes the form of a burning sensation, queasiness or even disgorgement. One such hygroscopic pharmaceutical material is an exogenously acidified antacid composition having cytoprotective properties described in co-pending application Ser. No. 831,756, filed Feb. 20, 1986, and now abandoned, of Gulan N. Mir et al incorporated herein by reference in its entirety. That application discloses, for example, an exogenously acidified aluminum base, i.e. magaldrate antacid composition wherein the magaldrate is acidified to a pH at which the magaldrate is solubilized and wherein the acidified composition contains about 50 to about 98 grams of precursor magaldrate per 100 milliliters of acidified composition. Such a composition has been found to exhibit gastric cytoprotective properties when administered orally to animals as a liquid or as a spray dried powder. In some instances, however, administration of the acidified antacid composition in the form of a spray dried powder enclosed in a gelatin capsule to animals, such as dogs, has resulted in stomach upset and disgorgement of the medication.

DESCRIPTION OF THE INVENTION

It has now been found that a safe and effective composition can be formulated from a solid hygroscopic pharmaceutical material which tends to cause disturbances in the balance of the gastrointestinal tract when administered orally to animals by admixing the solid hygroscopic pharmaceutical material with at least a partially hydrogenated and/or solidified vegetable oil and enclosing the admixture in a gelatin capsule.

DETAILED DESCRIPTION OF THE INVENTION

The formulations containingg solid hygroscopic pharmaceutical materials of the invention contain about 2% to about 30% by weight pharmaceutical material based on the total formulation weight. A smaller amount of the solid hygroscopic pharmaceutical material may not be a pharmaceutically effective amount and a larger amount may not be sufficiently protected.

Suitable solid hygroscopic pharmaceutical materials in addition to acidified antacid compositions include aspirin, aluminum hydroxide gel, ampicillin sodium, ampicillin trihydrate, and cephalexin. Mixtures of such hygroscopic pharmaceutical materials, such as aspirin with acidified antacid compositions, can be used in the formulations of this invention, as well as mixtures of hygroscopic pharmaceutical materials with non-hydroscopic pharmaceutical materials, such as ibuprofen, acetaminophen, ranitidine and azulene, can be employed.

Suitable at least partially hydrogenated and solidified vegetable oils include CRISCO® brand of hydrogenated vegetable oil, hydrogenated soybean oil, hydrogenated palm oil, hydrogenated cotton seed oil, hydrogenated corn oil, hydrogenated rapeseed oil, hydrogenated peanut oil, hydrogenated olive oil and hydrogenated castor oil, hydrogenated cocoanut oil, or cocoa butter and the like. Such at least partially hydrogenated and/or solidified vegetable oils should have a melting point below about 125° C. so that the solid hygroscopic pharmaceutical material is released in the gastric tract for absorption by the gastric mucosa.

In addition to the medicament and the at least partially hydrogenated and/or solidfied vegetable oil, the formulations can contain in minor amounts the customary excipients such as coloring agents, surfactants, preservatives, gelling agents, etc. The invention is further described by reference to the following examples.

EXAMPLE I

A formulation of the invention was prepared using an exogenously acidified magaldrate composition. This exogenously acidified magaldrate composition was prepared in general accordance with Example 17 of Mir et al patent application Ser. No. 831,756 filed Feb. 20, 1986 except that larger quantities were used and a Niro Portable Spray Dryer, manufactured by Niro Atomizer Inc., of Columbia, Maryland, was employed.

A sample of magaldrate gel, which had been spray dried to manufacture commercial magaldrate tablets, in the amount of 771.44 grams (84% magaldrate) was admixed in a stainless steel mixing tank with 1310 milliliters of 10 N hydrochloric acid and 2400 milliliters of purified water. The resulting solution was charged to the Niro Portable Spray Drier operated at an inlet temperature of 250° C. and an outlet temperature of 150° C. to provide a fluffy white powder.

A portion of the acidified magaldrate, in the amount of 18.33 grams, was blended into 100 grams of melted CRISCO® brand partially hydrogenerated vegetable shortening to provide a fomulation containing 15% by weight on a dry basis of acidified magaldrate based upon the total formulation. Dosage forms were prepared from this formulation by introducing 2.25 ml. of the formulation melt into a No. 13 hard gelatin capsule and cooling. Each dosage form contained about 359 milligrams of medication.

EXAMPLE 2

Another formulation of the invention was prepared using another portion of the acidified magaldrate used in Example 1. In this example, 18.33 grams of the acidified magaldrate were blended into 100 grams of melted pharmaceutical grade cocoa butter to provide a formulation containing 15% by weight on a dry basis of acidified magaldrate based upon the total formulation. Dosage forms were prepared from this formulation by introducing 2.25 ml. of the formulation melt into a No. 13 hard gelatin capsule and allowing to cool. Each dosage form contained about 396 milligrams of medication.

EXAMPLE 3

Another formulation was prepared using another portion of the acidified magaldrate used in Example 1. In this example, 18.33 grams of the acidified magaldrate were blended into 100 grams of melted commercial grade propylene glycol monostearate to provide a formulation containing about 15% by weight on a dry basis of acidified magaldrate based upon the total formulation. Dosage forms were prepared from this formulation by introducing 2.25 ml. of the formulation melt into a No.13 hard gelatin capsule. Each dosage form contained about 407 milligrams of medication.

The use of surfactants in the formulations of this invention is particularly advantageous since they assist in providing a homogenous formulation of acidified antacid and hydrogenated vegetable oil and aid in release of the acidified antacid in the gastric tract. Particularly suitable surface active agents include the non-ionic surfactants such as Tween-20.

EXAMPLE 4

The formulations of Examples 1–3 were tested for cytoprotective activity in rats. The pharmacological test used was the ethanol-induced lesion assay test in which animal studies show that cytoprotective compounds will prevent gastric lesions induced by oral administration of ethanol. The ethanol-induced lesion assay is a standard test for cytoprotective activity and is described in an article by A. Robert et al entitled "Cytoprotection By Prostaglandins in Rats" published in Gastroenterology 77:433–443,1979.

Male Sprague-Dawley rats weighing between 120–150 grams were used. the rats were fasted for 24 hours prior to use with water ad libitum. Animals were each orally pretreated, after separation into three groups, with the formulations of Examples 1,2 and 3 one hour before ethanol administration.

The effective dose in the rat to give 100% inhibition in the ethanol induced lesion assay test had previously been determined to be about 250 milligrams of acidified magaldrate per kilogram of rat body weight. Hence, the formulations were modified to provide about 3.5 milligrams acidified magaldrate per milliliter of melted formulation and each rat was fed 1 ml of melted formulation per 100 grams of body weight to provide a dose of about 250 mg/kg.

Absolute ethanol was administered orally to each rat, 1 milliliter per rat, intragastrically. One hour after ethanol administration the rats were sacrificed by carbon dioxide asphyxiation. The stomachs were removed and kept moist with saline until the lesions were scored. Ulcers were graded according to the following scale.

| Grade | Description Approximate Lesion Length |
|---|---|
| 0 | No lesion |
| 1 | 2 mm or less |
| 2 | 4 mm |
| 3 | 6 mm |

The mean ulcer source of each treatment group was expressed as the percent inhibition of ulcer formation. The results are shown below:

| Formulation | Dose* | % Inhibition |
|---|---|---|
| Example 1 | 250 | 89 |
| Example 2 | 250 | 65 |
| Example 3 | 250 | 30 |

*Dose in milligrams/kilogram of acidified magaldrate

EXAMPLE 5

The capsule dosage forms of Examples 1,2 and 3 were administered to dogs which had previously been fasted for 18 hours. The dogs were fed sufficient capsules based on their weight to provide a dose of about 200 milligrams of acidified magaldrate per kilogram of dog weight. The experiment was designed to determine whether the 200 mg/kg dose would induce vomiting in the dogs. The results are as follows:

| Formulation | Dose | Number of Dogs Vomiting |
|---|---|---|
| Example 1 | 200 | 1 of 3 |
| Example 2 | 200 | 0 of 2 |
| Example 3 | 200 | 0 of 3 |
| Placebo* | 200 | 6 of 6 |

The data show that the partially hydrogenated and/or solidified vegetable oils, i.e. CRISCO and cocoa butter protected the acidified magaldrate in the formulations from moisture, that the acidified magaldrate in the formulation retained its cytoprotective properties, and that the formulations reduced the tendency to disgorge the medication.

EXAMPLE 6

Another formulation of the invention was prepared using another portion of the acidified magaldrate used in Example 1. In this example, 21.428 grams of the acidified magaldrate were blended into 50.0 grams of melted All-Purpose Shortening supplied by Archer-Daniels Midland of Decator, Ohio, a partially hydrogenated vegetable shortening, to provide a formulation containing 30% by weight on a dry basis of acidified magaldrate based upon the total formulation. Dosage forms were prepared from this formulation by introducing 0.5 ml. of the formulation melt into a No. 13 hard gelatin capsule and cooling. Each dosage form contained about 122 milligrams of medication.

We claim:

1. A pharmaceutical cytoprotective dosage form for oral administration comprising a hard gelatin capsule encapsulating an admixture consisting essentially of (i) about 2% to about 30% by weight of the admixture of a spray dried solid hygroscopic cytoprotective powder, the powder having been formed by spray drying an exogenously acidified aluminum base composition wherein the aluminum base composition is acidifed to a pH at which the aluminum base composition is solubilized and wherein the resulting acidified composition contains about 50 to about 98 grams of precursor aluminum base composition per 100 milliliters of acidified composition, the powder being blended into (ii) an at least partially hydrogenated and/or solidified vegetable oil having a melting point below about 125° C.

2. A pharmaceutical cytoprotective dosage form of oral administration comprising a hard geletin capsule encapsulating an admixture consisting essentially of (i) about 2% to about 30% by weight of the admixture of a spray dried solid hygroscopic cytoprotective powder the powder having been formed by spray drying an exogenously acidified magaldrate composition wherein the magaldrate composition is acidified to a pH at which the magaldrate is solubilized and wherein the resulting acidified magaldrate composition contains about 50 to about 98 grams of precursor magaldrate composition per 100 milliliters of acidfied composition, the powder being blended into (ii) an at least partially hydrogenated and/or solidified vegetable oil having a melting point below about 125° C.

3. The dosage form of claim 2 wherein the partially hydrogenated and/or solidified vegetable oil is a partially hydrogenated and solidified mixture of soybean oil and palm kernel oil.

4. The dosage form of claim 3 wherein the admixture contains about 10% to about 20% by weight of the spray dried cytoprotective powder.

5. The dosage form of claim 1 additionally containing a surface active agent.

6. The dosage form of claim 1 additionally containing a solid non-hygroscopic medicinal substance.

7. The dosage form of claim 4 additionally containing a surface active agent.

* * * * *